United States Patent
Batsman et al.

(10) Patent No.: US 11,813,053 B2
(45) Date of Patent: Nov. 14, 2023

(54) METHOD AND SYSTEM FOR PREDICTING PATIENT RECOVERY TIME FROM NEUROMUSCULAR BLOCK

(71) Applicant: GE Precision Healthcare LLC, Wauwatosa, WI (US)

(72) Inventors: Helena Liisa Anneli Batsman, Espoo (FI); Kimmo Henrik Uutela, Helsinki (FI); Markku Erik Spoof, Tuusula (FI)

(73) Assignee: GE Precision Healthcare LLC, Wauwatosa, WI (US)

(*) Notice: Subject to any disclaimer, the term of this patent is extended or adjusted under 35 U.S.C. 154(b) by 965 days.

(21) Appl. No.: 16/536,553

(22) Filed: Aug. 9, 2019

(65) Prior Publication Data

US 2021/0038120 A1   Feb. 11, 2021

(51) Int. Cl.
*A61B 5/11* (2006.01)
*A61B 5/00* (2006.01)

(52) U.S. Cl.
CPC .......... *A61B 5/1106* (2013.01); *A61B 5/7275* (2013.01)

(58) Field of Classification Search
CPC ... A61B 5/1106; A61B 5/7275; A61B 5/6877; A61B 5/395; A61B 5/00; A61B 5/103; A61B 5/11; A61B 5/1104; A61P 21/00
See application file for complete search history.

(56) References Cited

U.S. PATENT DOCUMENTS

| | | | |
|---|---|---|---|
| 8,506,502 B2* | 8/2013 | Gilhuly | A61B 5/746 600/554 |
| 2009/0327204 A1* | 12/2009 | Gilhuly | G05B 17/02 703/2 |
| 2019/0223764 A1* | 7/2019 | Hulvershorn | A61B 5/296 |

OTHER PUBLICATIONS

Lendl M. et al. Nonlinear Model-Based Predictive Control of Non-Depolarizing Muscle Relaxants Using Neural Networks Journal of Clinical Monitoring and Computing, (1999) 15, 271-278.
Santanen O. et al. Neural nets and prediction of the recovery rate from neuromuscular block. European Journal of Anaesthesiology, (2003) 20(2), 87-92.
Unpublished U.S. Appl. No. 15/988,176 to Markku Erik Spoof, filed May 24, 2018.

* cited by examiner

*Primary Examiner* — Patrick Fernandes

(57) ABSTRACT

A method and system for monitoring neuromuscular blockade in patients during surgical procedures. A stimulator provides stimulation to a nerve of the patient, such as train-of-four (TOF). Following such stimulation, the system and method creates a predicted recovery trend for the patient that is based upon measured recovery trend and a recovery model. The recovery model estimates a recovery trend for the patient based on initial model parameter values. The recovery model creates a predicted recovery trend that is used to estimate a recovery time for the patient. The trend values from the patient are monitored and compared to the predicted trend values throughout the operation as long as the NMT measurement is on. During recovery, the recovery model and recovery time estimates are updated based on the recovery trend being formed from measurements of the patient.

19 Claims, 12 Drawing Sheets

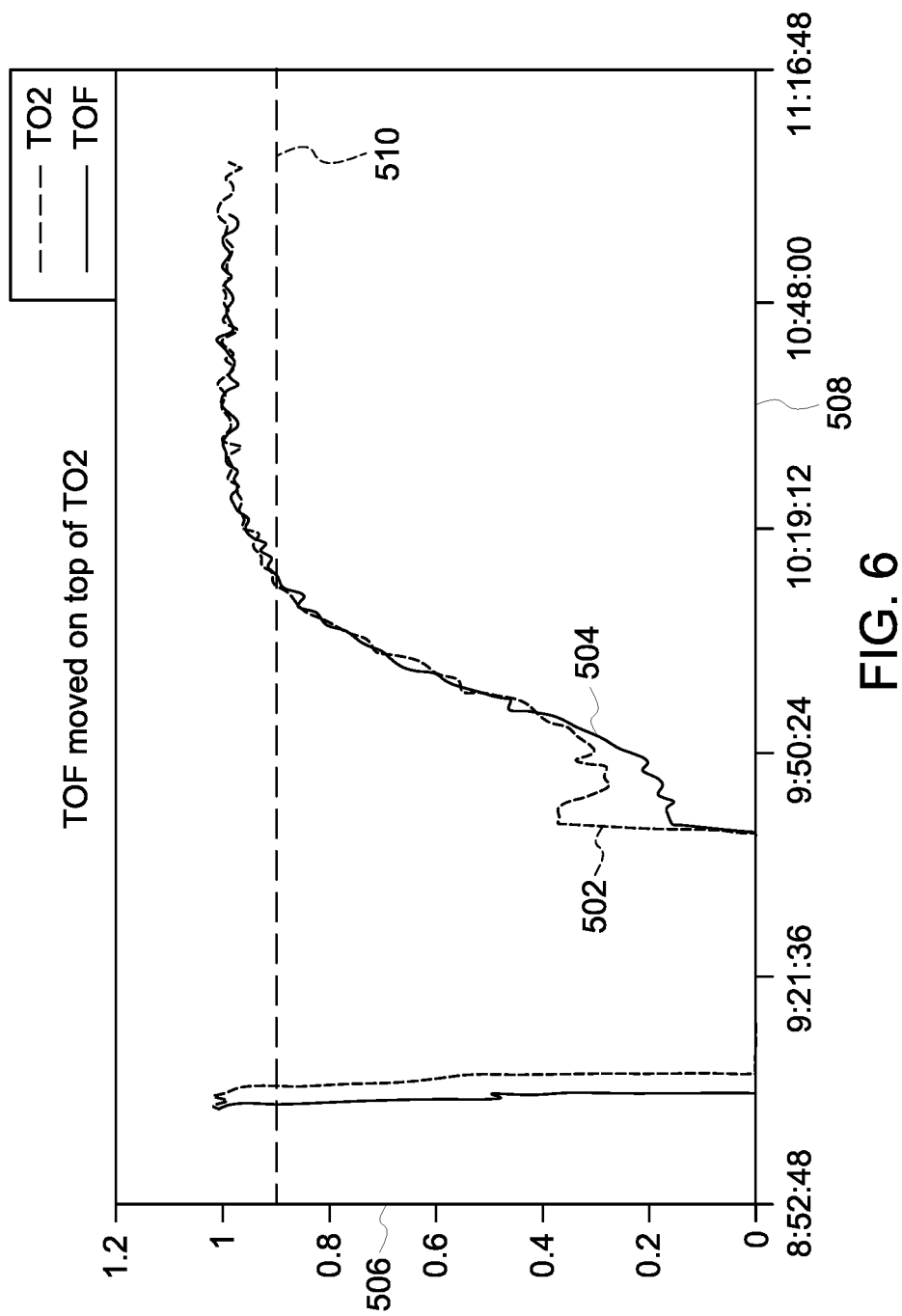

METHOD AND SYSTEM FOR PREDICTING PATIENT RECOVERY TIME FROM NEUROMUSCULAR BLOCK

FIELD

The present disclosure relates to medical devices, and more particularly, to medical devices and methods of operating medical devices for monitoring neuromuscular transmission during a surgical procedure.

BACKGROUND

Neuro Muscular Transmission (NMT) is the transfer of an impulse between a nerve and a muscle in the neuromuscular junction. NMT may be blocked in a patient undergoing a surgical procedure, for example, by neuromuscular blocking agents/drugs, which may cause transient muscle paralysis and prevent the patient from moving and breathing spontaneously.

Muscle relaxation is used during general anesthesia to enable endotracheal intubation and to provide the surgeon with optimal working conditions. At the end of a surgical procedure, the level of NMT is used to determine when the patient can be extubated. Thus, the level of neuromuscular block may be monitored to ensure appropriate block is provided for the given procedure and to determine when the patient can be safely extubated.

SUMMARY

In one embodiment, a method to estimate recovery time of a patient from a neuromuscular block includes applying a first TOF stimulation to a nerve of the patient at a first measurement time. First, second, third and fourth muscle twitches are measured in response to the first TOF stimulation. A second TOF stimulation is applied to the nerve of the patient at a second measurement time and the muscle twitches in response to the second TOF stimulation are measured. Based upon the muscle twitches in response to the first and second TOF stimulations, the method determines if the patient is beginning to recover and if recovery has started, calculates a predicted recovery trend and an estimated recovery time based on the predicted recovery trend. The estimated recovery time is provided to a clinician.

In one embodiment, the estimated recovery time is calculated by creating a predicted recovery trend based on a recovery model that is initialized based upon initial model parameter values that are drug and patient independent. The predicted recovery trend extrapolates from the measured muscle response ratios, such as TOF ratios, to estimate the recovery time when the TOF ratio will exceed a predefined level. The predicted recovery trend can be calculated utilizing different algorithms or recovery models that involve either measured parameters from the patient or are based upon historic patient trends. In one exemplary embodiment, the recovery model is based on a sigmoid function, although other recovery prediction models are contemplated. Regardless of the recovery prediction model used, the predicted recovery trend presents an estimated recovery time at which the intubation tube can be removed from the patient and the patient can breathe spontaneously.

During recovery of the patient after the predicted recovery trend is initially calculated based upon initial model parameter values and measurements from the patient, the system and method continues to monitor both the TOF and TO2 ratios and trend values derived from muscle response ratios obtained from the patient. The measured trend values are compared to predicted trend values that are initially based on historical patient data and that can be updated with the measurements obtained from the ongoing patient case. If there has not been a sudden change in the monitored trend values, the method and system of the present disclosure modifies the estimated recovery time and updates the recovery model by fitting the model with the measured ratios and calculates a new predicted recovery time. Alternatively, the method and system to estimate recovery time can restart the recovery prediction process if the system determines that it is otherwise necessary or if an NMBA is applied to the patient. If the method determines that a reverse NMBA is administered to the patient, the system and method terminates operation since the patient is rapidly recovering from the blocking agent. Alternatively, the system could select a different recovery model, such as a linear model, that better represents recovery after the administration of the reverse NMBA.

By continuing to monitor the recovery trend of the patient and comparing the monitored recovery trend to a predicted recovery trend, it is possible to react to changes in the recovery trend. The changes in the recovery trend can result from many reasons, such as from NMBA or reverse NMBA being given to the patient. Depending on the case, it is possible to start, continue, pause or restart the recovery prediction process (RPP) needed to predict the recovery time. For example, if a reverse NMBA is detected, the recovery prediction process is ended because of a sudden rise in the muscle response measurements. Ending the process can also be possible if more NMBA is given to the patient, resulting in a decrease in measured muscle responses. Once the responses start to increase again, thereby indicating the start of recovery, the recovery prediction process can be started again.

In another embodiment, the system and method calculates the predicted recovery trend based upon ratios obtained from the patient prior to the restart of the recovery prediction process. Utilizing previously obtained ratios from the patient allows the method and system of the present disclosure to improve the predicted recovery trend.

In another embodiment, a medical device for multi-parameter monitoring of a patient includes a stimulator to apply train-of-four stimulation to a nerve of the patient. An electromyography (EMG) sensor or other type of sensor detects first, second, third and fourth muscle twitches in response to the TOF stimulation. A controller is operable to create a predicted recovery trend that is based upon the detected muscle twitches as well as other data, such as historic patient trends. The medical device includes a display that visually displays the predicted recovery trend along with measured muscle response measurements, such as TOF ratios. The controller monitors the measured muscle response ratios and trend values and adjusts both the recovery prediction process and the predicted recovery trend and recovery time estimate as needed.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 6 is a graph similar to FIG. 5 in which the TOF trend is moved on top of the TO2 trend;

DETAILED DESCRIPTION

The following description relates to various embodiments of a neuromuscular transmission (NMT) monitoring system configured to monitor an amount of neuromuscular blockage after the administration of a neuromuscular blocking agent (NMBA) or muscle relaxants in patients during surgery. Neuro Muscular Transmission (NMT) is the transfer of an impulse between a nerve and a muscle in the neuromuscular junction. NMT may be blocked by neuromuscular blocking agents (NMBA), which may cause transient muscle paralysis and prevent the patient from moving and breathing spontaneously. Additionally, muscle relaxation may be used during general anesthesia to enable endotracheal intubation and to provide the surgeon with optimal working conditions. At the end of a surgical procedure, the neuromuscular block is reversed such that neuromuscular activity may be returned to normal and that the patient may be able to breathe unassisted, before the removal of the endotracheal intubation (i.e. extubation). Thus, appropriate assessment of the degree of NMT block may be used for ensuring proper timing of intubation and for guiding intraoperative administration of neuromuscular blocking agents, maintaining a desired degree of intraoperative neuromuscular block, and ultimately preventing the occurrence of residual muscle paralysis.

An NMT monitor may be used to monitor muscle response to electrical stimulation of a motor nerve (e.g., ulnar nerve). For example, an electrical stimulus may be provided at the ulnar nerve near the wrist and the response of the muscle near the thumb, adductor pollicis, may be monitored. In clinical settings, a nerve stimulator is attached to on top of a motor nerve of the patient and an electrical stimulation current is applied to the patient before induction of anesthesia. A reference value for the muscle response is recorded by the NMT monitor and used to normalize the muscle response once the muscle relaxant is administered. The evoked muscle responses may then be monitored through the measurement of electrical response of the muscle (electromyography (EMG)). In EMG, multiple electrodes may be used to record the compound muscle potential stimulated by the stimulus generator.

According to embodiments disclosed herein, neuromuscular transmission monitoring may be performed by measuring the electrical potentials at the muscle via an electromyography (EMG) sensor, in response to an electric stimulation of a motor nerve.

Figure 1:
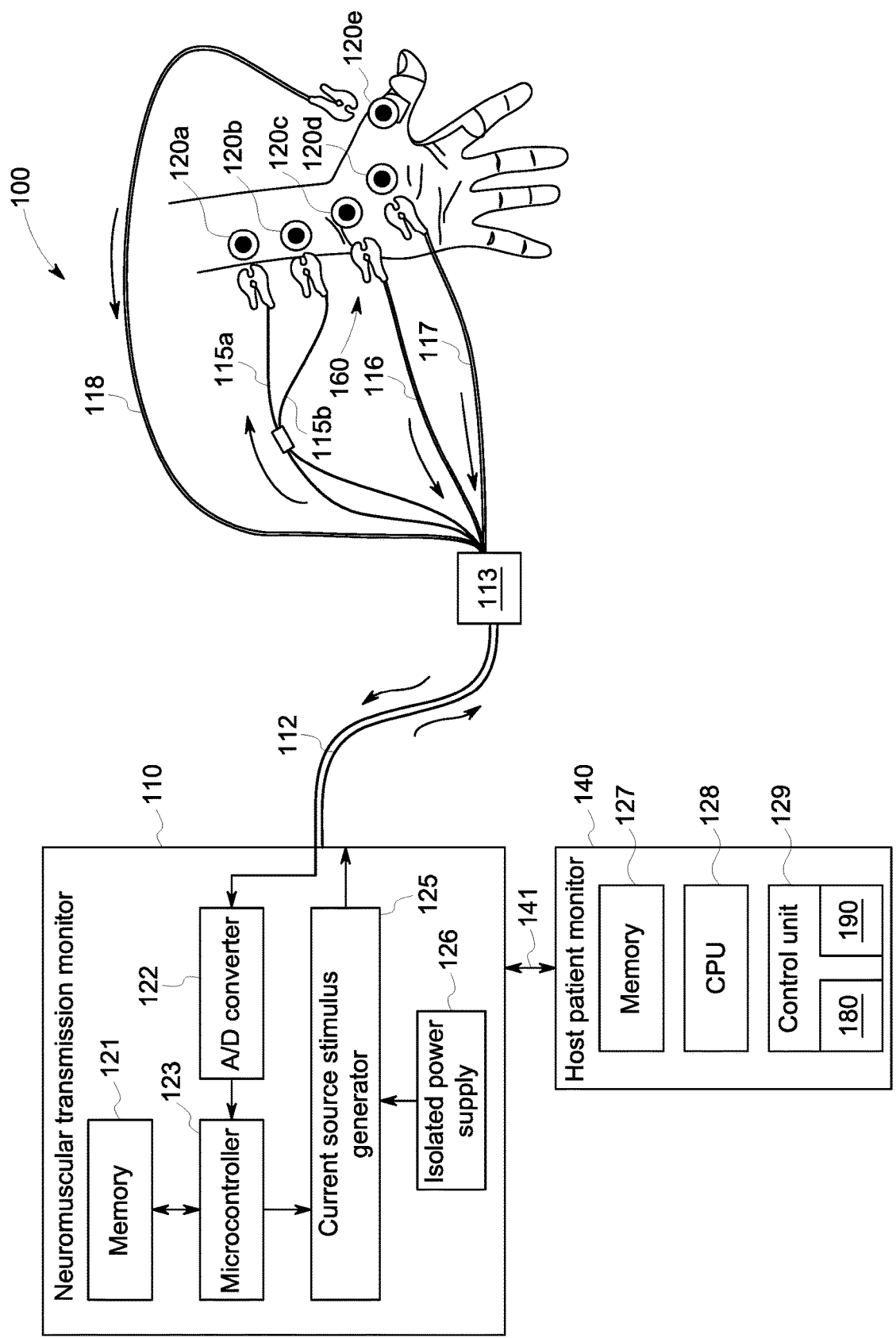
FIG. 1 shows an example neuromuscular transmission monitoring system.

An example of a neuromuscular transmission monitoring system is provided in FIG. 1. The NMT monitoring system may include one or more electro-sensors which detect electrical activity of a muscle (referred to as an EMG sensor) in response to nerve stimulation, and a nerve stimulator. The NMT monitoring system of FIG. 1 also includes a computing system including instructions to carry out one or more control routines for determining a muscle response baseline as well as monitoring neuromuscular block in patients during surgery and post surgery during recovery.

FIG. 1 illustrates an example neuromuscular transmission (NMT) monitoring system 100 that is configured to monitor neuromuscular activity via EMG techniques. NMT monitoring system 100 includes a neuromuscular transmission monitor 110 which is communicatively coupled to a host patient monitor 140 via a communication link 141. The neuromuscular transmission monitor 110 includes a plurality of neurostimulators, 115a and 115b, for providing stimulation output (e.g., electrical stimuli) of varying type and frequency to the patient and at least one input connected to one or more transducers for monitoring the evoked muscle response in response to the electrical stimuli provided by the neurostimulators. The transducers include an EMG sensor 160 consisting of a plurality of electro-sensors for measuring the action potential of muscle contraction in response to nerve stimulation. The signals detected by the transducers may then be converted into electrical signals by the A/D converter 122 of neuromuscular transmission monitor 110.

In the depicted example, neurostimulators 115a and 115b are connected to stimulating electrodes 120a and 120b, respectively, which may apply an electrical stimulus to the patient's ulnar nerve at a pre-determined time interval. The amount of electrical stimulation provided to the neurostimulators is controlled by a current stimulus generator which receives command signals from microcontroller 123. Microcontroller 123 is linked to the user interface of control unit 129, which comprises of a display unit 190 and buttons/knobs 180. The type and frequency of the stimulation output may be adjusted manually by the user (manual mode) or be automatically chosen by the system (automatic mode). In one example, the type and frequency of the stimulation output may be adjusted by the user via pressing buttons or knobs 180 on the patient host monitor 140. In one example, neurostimulators 115a and 115b may be two wires of positive and negative charges, which may be attached by alligator clips to stimulating electrodes 120a and 120b on the skin of the patient's forearm.

A power supply (not shown) may supply electricity to an isolated power supply 126 which in turn provides power to current source stimulus generator 125. The microcontroller 123 may be connected to the current source stimulus generator 125 to adjust the amount of electric current provided to the neurostimulators 115a-b. The current stimulus generator 125 may generate different types of neurostimulation including train-of-four (TOF), single twitch (ST), double burst (DBS), post tetanic count (PTC), current range (e.g., 1-70 mA with 1 mA steps), pulse width/frequency (e.g., 100, 200, 300 µs, or 1 Hz, 2 Hz, etc.). Further, the types of neurostimulation may be chosen via a manual or an automatic stimulating mode. If a manual stimulating mode is chosen, then the user may input the desired neuromuscular stimulating types, current range, and pulse width and/or frequency via pressing button 180 of the host patient monitor 140, for example. Alternatively, if a touch-screen is used as the display unit (e.g., display unit 190 of host patient monitor 140), then user input may be provided via touch input to the touch-screen on the display unit.

If an automatic neurostimulation mode is chosen, microcontroller 123 of neuromuscular transmission monitor 110 may select a first neurostimulation type as its default setting, such as TOF stimulation, and based on the muscle response signals received from the EMG sensors, the microcontroller reports the muscle response signals to the user by displaying graphs and numbers (e.g., via display unit 190 of host patient monitor 140). The display unit 190 may display the muscle response data/information to the user and may also include alarm signals/message for alerting the user of potential sensor error.

Additionally, neuromuscular transmission monitor 110 may be connected to a host patient monitor 140 through a communication link 141. Host patient monitor 140 may include memory 127, CPU 128, and control unit 129. Memory 127 may have similar functions as memory 121. Control unit 129 may include control buttons/knobs 180 and display unit 190. The control buttons and knobs of control unit 129 may be configured to allow for user input. The display unit 190 may be configured to receive touch input from a user.

The preferred neuromuscular stimulating output of the present disclosure is a train-of-four (TOF). In one example, TOF may typically use four brief (between 100 and 300 µs) current pulses (generally less than 70 mA) at 2 Hz, repeated every 10 to 20 s as electrostimulation. The resulting twitches (i.e. muscle response) may be measured and quantified for electromyographic response via the EMG sensor. The first twitch (referred to as the T1 twitch) and the last twitch (referred to as the T4 twitch) are compared and the ratio of the last twitch to the first twitch (referred to as TOF ratio) may provide an estimate of the level of neuromuscular blockade (e.g., depth of relaxation) experienced by the patient. The TOF ratio may range from 0 to 100%, for example. The electrical TOF stimuli series may be spaced by ten or more seconds (generally 20 s is used to provide a margin of safety) to give a rest period for full restoration of steady state conditions, as faster stimulation results in smaller evoked responses. TOF stimulation is the most commonly used technique for monitoring the neuromuscular blockade in lightly-blocked patients as well in patients that are recovering from neuromuscular block.

In addition to the TOF ratio, another ratio that can be calculated during TOF stimulation is referred to as TO2. TO2 is the ratio of the second twitch (T2) to the first twitch (T1) in the train-of-four stimulation pulses.

EMG sensor 160 may include a plurality of electro-sensing connections 116, 117, and 118 connected to sensing electrodes 120c, 120d, and 120e, respectively. Most commonly, the three sensing electrodes are positioned to give the most consistent EMG signals. In the depicted example, sensing electrode 120e is placed over the muscle tendon or finger, sensing electrode 120d is placed over the mid-portion of the muscle close to the neuromuscular junction, while sensing electrode 120c may be variable. In one example, electrodes 120d and 120e may be recording electrodes, while electrode 120c may be a grounding electrode. The grounding electrode provides a common reference for the EMG recording electrodes. For example, the recording electrode 120d may be placed on top of m. adductor pollicis in the thenar eminence and recording electrode 120e may be placed on top of the distal interphalangeal joint of the thumb, while the grounding electrode 120c may be placed at centerline over the flexor retinaculum at the palmar side of the wrist. EMG sensor 160 measures the magnitude of electrical activity sensed by electrodes 120c-120e in response to nerve stimulation and when received at the neuromuscular transmission monitor, is recorded as the EMG muscle response signal.

Stimulating electrodes 120a-120b and sensing electrodes 120c-120e may have mechanisms for improving electrical contact to skin such as ultrasound gel and mechanisms for improving fixation to the skin such as biocompatible adhesives placed beneath the electrodes. Further, the electrodes may be suitable electrodes, such as silver/silver chloride electrodes. Further, the electrodes may be disposable electrodes which can be discarded after a single use. In another example, the stimulators (e.g., stimulators 115a and 115b) and the sensing connections (e.g. electro-sensing connections 116-118, and mechano-sensing connection 114) along with their respective electrodes may be incorporated into a disposable sensing unit. In one example, the disposable sensing unit may be included as part of a one-size-fits-all stretchable glove which may be discarded after a single use.

Further, information regarding the EMG muscle response signals received from EMG sensor 160 may be sent to neuromuscular transmission monitor 110 via main connector 113 and cable 112. In one example, muscle response signals from EMG sensor 160 sensor are fed into a signal scaling and filtering circuit (not shown). After scaling the signal and filtering noise, the signal may be converted from an analog signal to a digital signal in analog-to-digital (A/D) converter 122 and sent to a microcontroller 123 for processing. Further, the muscle response signals may also be amplified via an amplifier (not shown) before being transmitted into the A/D converter 122. The microcontroller 123, or processing unit, is connected to a memory 121 and once the signals are processed, the signal data may be displayed on the display unit 190 of the host patient monitor. In one example, the processed signals may be transmitted to the host patient monitor 140 and displayed on the display unit 190 in real-time. Further still, the processed signals may be updated and stored in memory 121. Memory 121 may be a conventional microcomputer which includes: a central processing unit (CPU), a read-only memory (ROM), a random access memory (RAM), and a conventional data bus. Additionally, the memory may include an automatic calibration module to determine the optimum supramaximal current to provide to the patient based on the muscle response value received by the EMG sensors, and based on the raw signals received from sensors, the module may determine a value, which may be used as a reference value for the neuromuscular blockade monitoring in patient. Further, the automatic calibration module may only be performed when patient is not in paralyzed state. In other words, the automatic calibration module may utilize a reference value based on the signals received from the sensors when patient is in non-relaxed state (e.g., before the administration of the muscle relaxant).

Control unit 129 may also include a user interface (not shown) which can be used to control operation of the NMT monitoring system 100, including controlling the input of patient data, changing the monitoring parameters (e.g. stimulus type, current range, frequency/pulse width, etc.), and the like. The user interface may also include a graphical user interface configured for display on a display device, such as display unit 190. The graphical user interface may include information to be output to a user (such as muscle response signals, patient data, etc.) and may also include menus or other elements through which a user may enter input the control unit 129.

As discussed above, during neuromuscular stimulating of a patient to determine the depth of relaxation, train-of-four (TOF) stimulation is applied to the patient and the muscle response signals are received from EMG sensors for each of the four pulses of the stimulation. The TOF stimulation is applied to the patient at regular intervals, such as every 10-20 seconds and the resulting twitches (i.e. muscle responses) are measured and quantified for electromyographic response by the EMG sensor 160.

Figure 2:
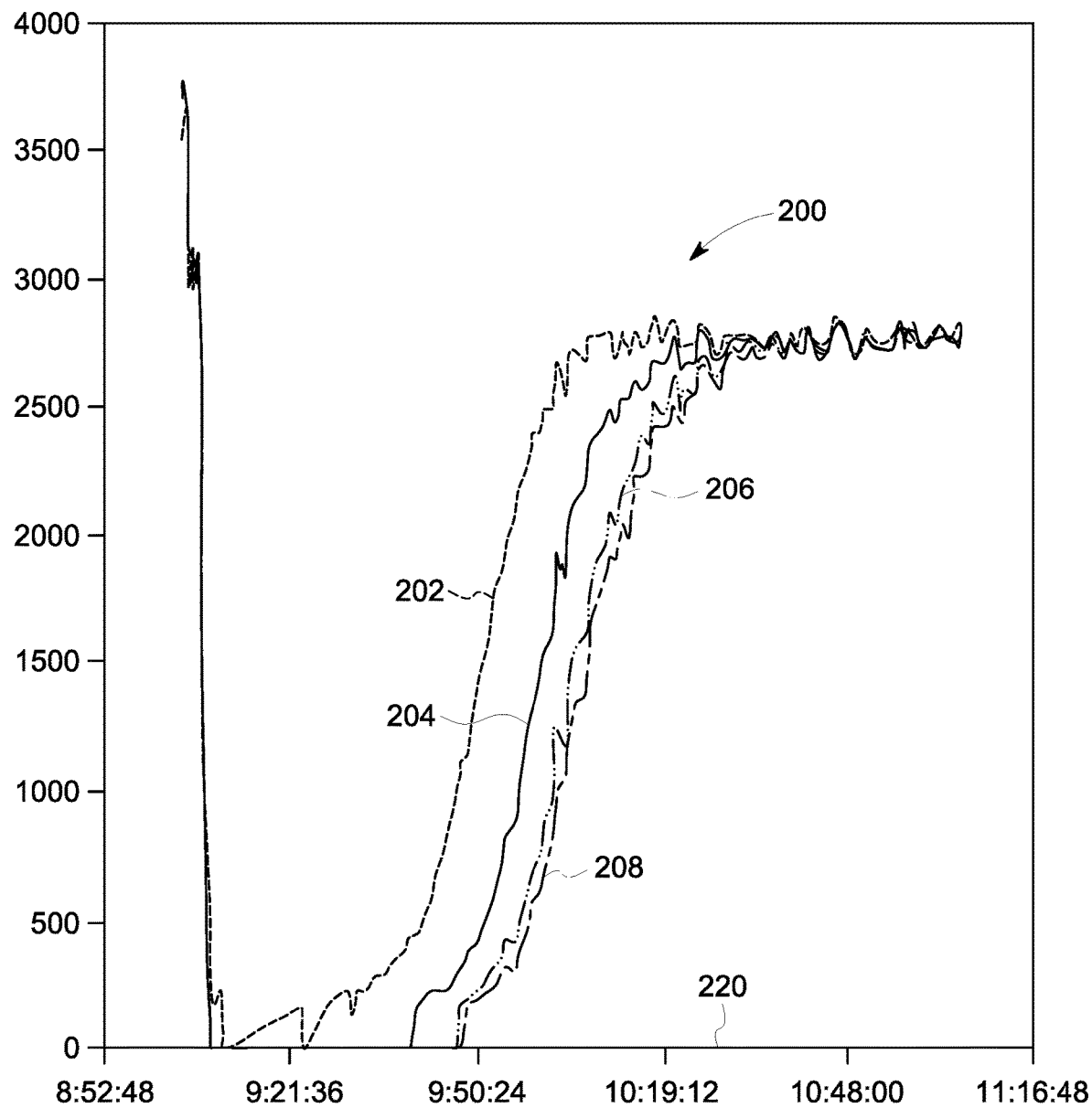
FIG. 2 is a graph showing the muscle twitch responses to a train-of-four (TOF) stimulation over time.

FIG. 2 illustrates exemplary EMG responses to each of the four pulses of a TOF stimulation over a measurement period set forth on the horizontal axis of the graph. The first twitch, referred to as the T1 twitch, is graphically illustrated by trace 202 in the graph 200. The second twitch, referred to as the T2 twitch, is shown by trace 204 while the third twitch, T3, is illustrated by trace 206. The last and final twitch, referred to as the T4 twitch, is shown by trace 208. As can be seen by the combined graph 200 of FIG. 2, the T1 trace 202 begins to be detected at the earliest point in time since the T1 twitch is in response to the first stimulation of the TOF stimulation sequence. The T2, T3 and T4 twitches begin to be detected at a time slightly delayed from the detection of the T1 twitch, as is well known for a patient recovering from the neuromuscular blocking agent.

In well-known recovery monitoring methods, extubation of the patient should only occur when the recovery of the patient reaches a recovery threshold at which the neuromuscular blocking has been diminished enough to insure proper spontaneous breathing by the patient. The recovery threshold is often based upon the ratio of the T4 twitch to the T1 twitch (T4/T1), which is commonly referred to the TOF ratio or TOF %. As described previously, the TOF ratio may range between 0 and 100%. Typically, when the TOF ratio reaches 90%, extubation of the patient is considered to be safe. Thus, the relationship between the T1 twitch and the T4 twitch is very important in determining when the patient can be safely extubated. As can be understood with respect to FIG. 2, the TOF ratio of 90% occurs when the T4 trace 208 begins to closely correspond to the T1 trace 202.

During currently available relaxation depth monitoring utilizing TOF stimulation, a clinician must continue to monitor the patient and wait for the TOF ratio to reach 90% or higher before removing the intubation tube. Although this type of monitoring has proven effective, it requires the clinician to continuously monitor the patient and wait for the TOF ratio to reach the desired value. This requires the clinician to sometimes wait for quite long time (20 minutes or more) while monitoring the TOF ratio.

Figure 3:
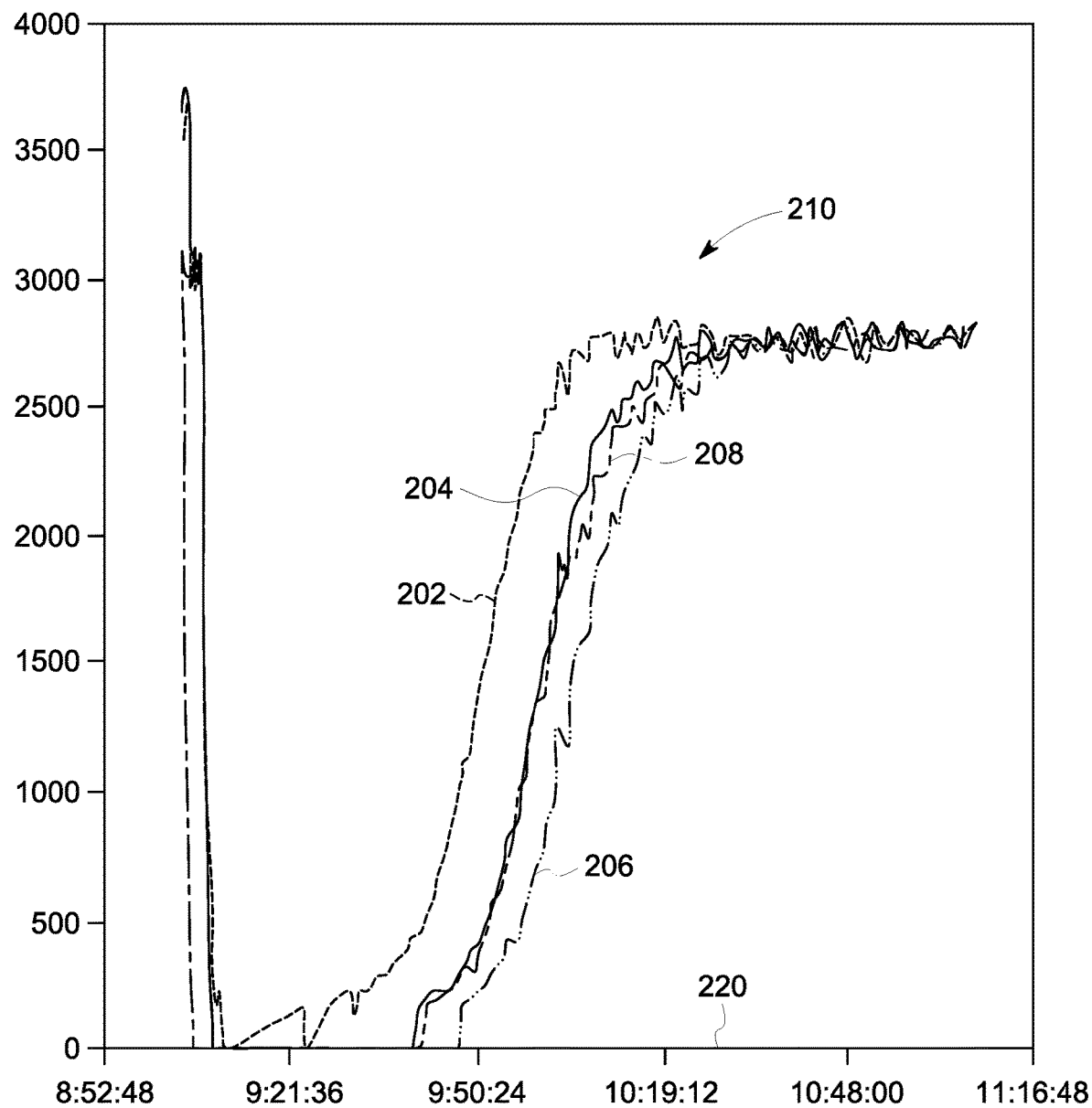
FIG. 3 is a graph showing the muscle twitch response twitches with T4 moved on top of T2.
Figure 4:
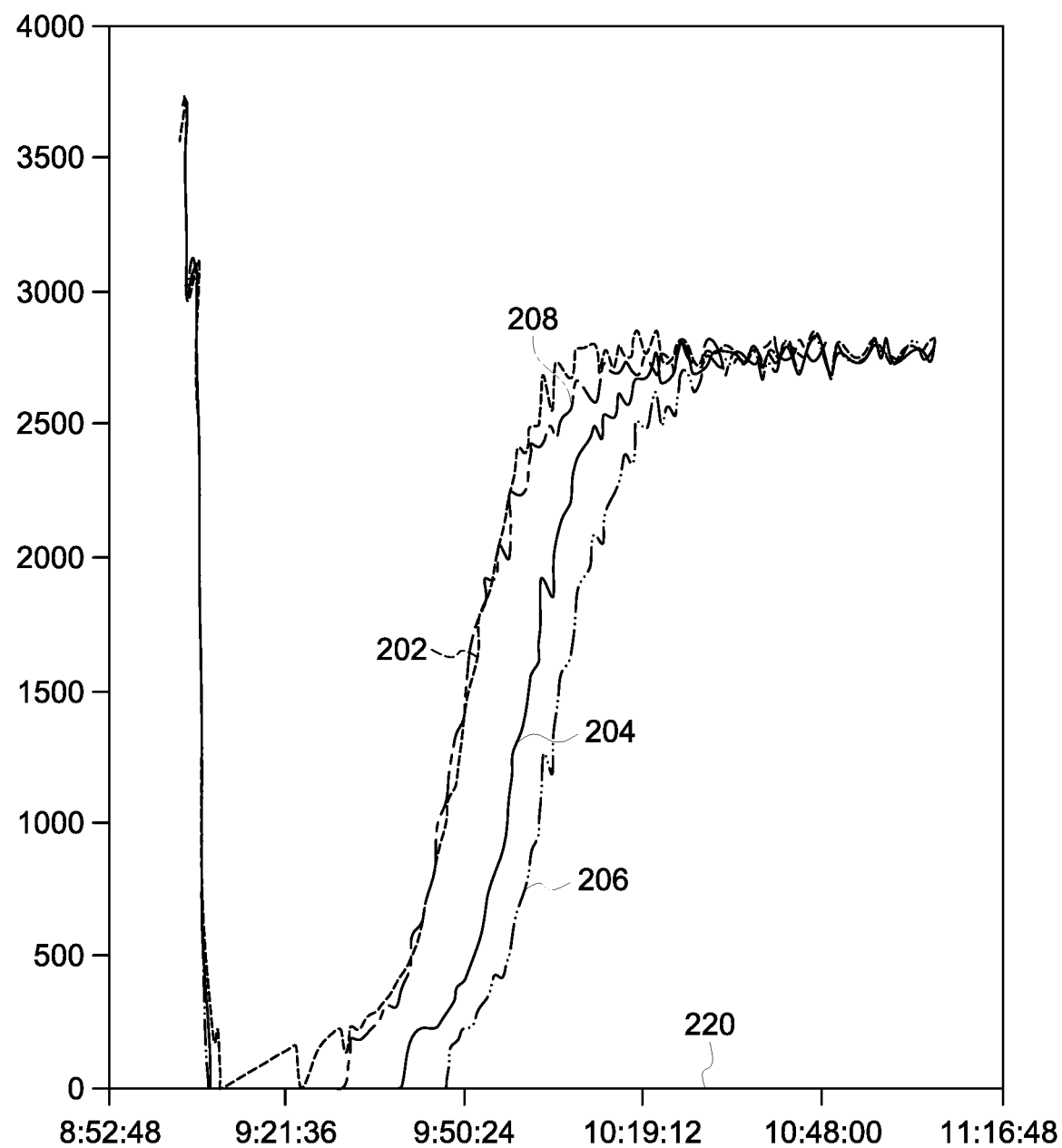
FIG. 4 is a graph showing the muscle twitch response twitches with T4 moved on top of T1.

Referring now to FIG. 3, graph 210 illustrates the similarity in shape between the T2 trace 204 and the T4 trace 208 by superimposing the T4 trace 208 onto the T2 trace 204. Since the T1 trace occurs sooner than the T4 trace when monitoring the patient, the inventor has recognized that the shape of the T1 and T2 traces can be used to predict the shape of the T4 trace and can be used as an estimate for determining when the TOF ratio will reach the 90% threshold. FIG. 4 provides further evidence that the T4 trace 208 closely matches the T1 trace 202, which is evidenced by superimposing the T4 trace 208 onto the T1 trace 202.

Figure 5:
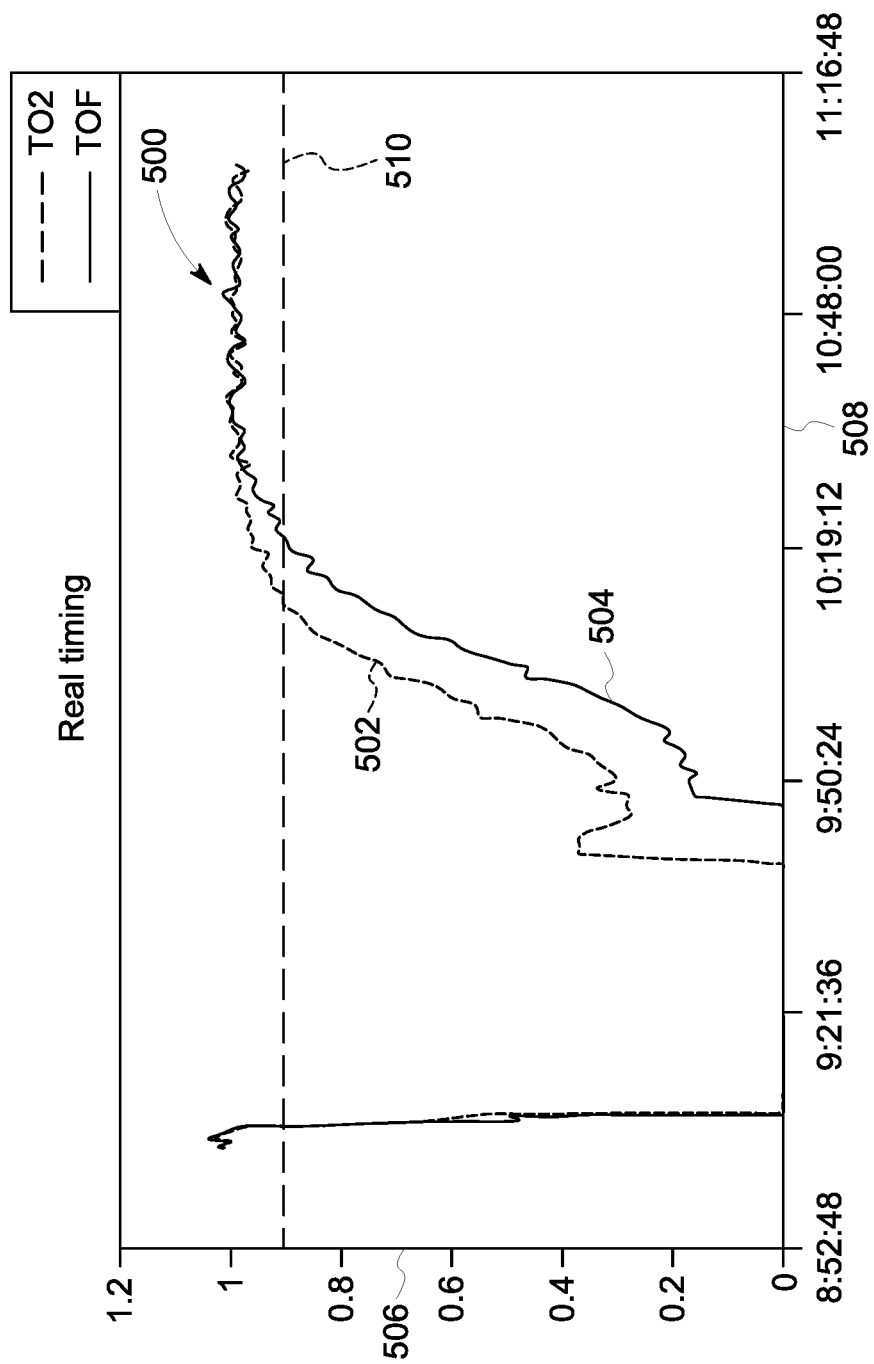
FIG. 5 is a graph showing the TO2 and TOF ratios over time.

Referring now to FIG. 5, graph 500 illustrates two separate ratios that are calculated from a representative patient. The first ratio, which is referred to as the TO2 ratio, represents the ratio of the T2 trace to the T1 trace (T2/T1) and is shown by trend 502. The second trend 504 shown in FIG. 5 is the TOF ratio, which is the T4 twitch relative to the T1 twitch (T4/T1). In the graph 500 of FIG. 5, the vertical axis 506 is a ratio while the horizontal axis 508 is a time axis. As previously discussed, extubation of the patient typically occurs when the TOF ratio, represented by trend 504, exceeds a threshold 510, which in the embodiment of FIG. 5 is 90%. In the embodiment shown, the TOF ratio exceeds the threshold 510 at approximately 10:19. FIG. 6 is a graphic illustration of the correspondence in shape of the TOF ratio trend 504 to the TO2 ratio trend 502. The graphic representation shown in FIG. 6 illustrates that the TO2 trend can be used as an early representative estimate for the TOF trend, which will allow for a prediction of the time when the TOF trend 504 will exceed the threshold 510.

In accordance with the present disclosure, the microcontroller 123 shown in FIG. 1 is configured to provide an estimated recovery time for the patient, which represents a time in the future when the TOF ratio will exceed the extubation threshold, which is typically 90%. The estimated recovery time calculated by the microcontroller 123 can be displayed to the clinician through a display such that the clinician can make treatment decisions, such as either to allow the patient to recover as is occurring or the clinician can decide if an antidote, referred to as a reverse NMBA, is needed to accelerate the recovery process.

FIG. 7 illustrates several graphic displays taken over time based on clinical data. Each graphic display shows an estimated time of recovery calculated utilizing the system and method of the present disclosure. In FIG. 7A, a series of measured TOF ratios 702 are plotted along the time axis 704. As can be seen in FIG. 7A, the series of individual measured TOF ratios 702 begin to rise as the depth of relaxation lessens. In accordance with the present disclosure, a predicted recovery trend 706 is calculated and displayed along the time axis after the measured TOF ratios. In the embodiment shown in FIG. 7A, the estimated TOF will exceed 90% at the time of 10:21:16. This prediction was generated by the system at the time of 10:00:00 Thus, the clinician will have an estimated time of extubation approximately twenty-one minutes before the clinician would otherwise know this information if simply monitoring the changing measured values of the TOF ratio.

FIGS. 7B-7H illustrate further measurements 702 of the TOF ratio at later periods in time as plotted over the predicted recovery trend 706. As time passes, it can be seen in the graphs of FIG. 7 that the measured TOF ratios 702 closely match the predicted recovery trend 706 until FIG. 7H where the last measured TOF ratio 708 exceeds the recovery ratio threshold of 90%. In the embodiment illustrated, the estimated recovery time of 10:21:16, which was predicted at time 10:00:00 closely matched the actual time of 10:20:08 when the TOF ratio exceeded 90%. Thus, in the clinical data graphed and shown in FIG. 7, the method of the present disclosure was able to predict the estimated recovery time to a high degree of accuracy and provided this estimated recovery time to the clinician over twenty minutes before the TOF ratio reached the 90% threshold for extubation.

Figure 7A:
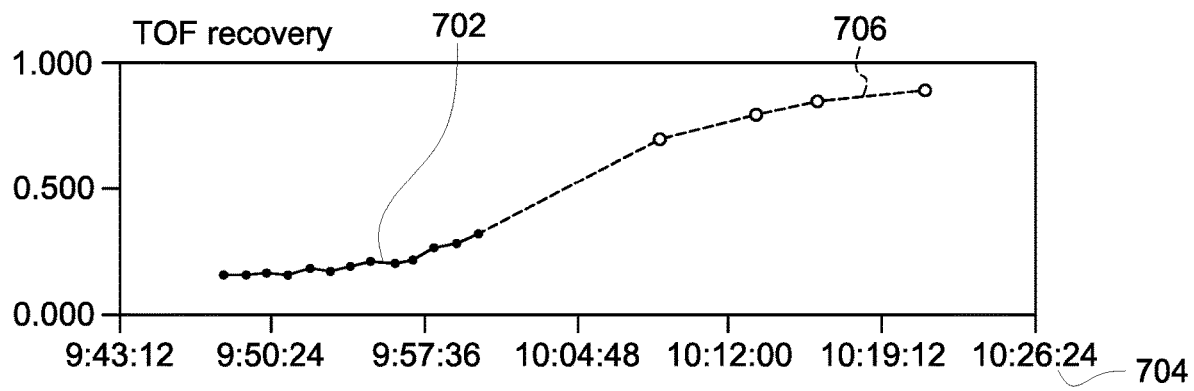
FIG. 7A-7H is a series of graphs showing the display of measured TOF ratios relative to a predicted recovery trend over time.
Figure 7B:
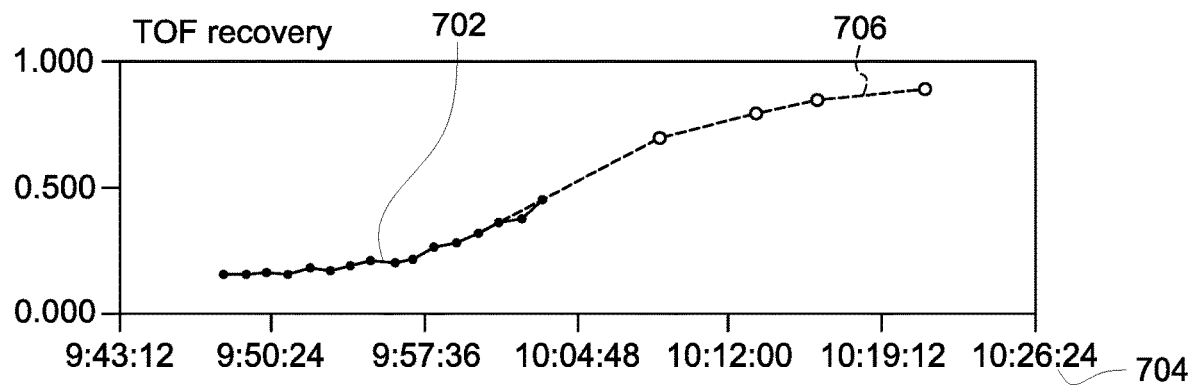
Figure 7C:
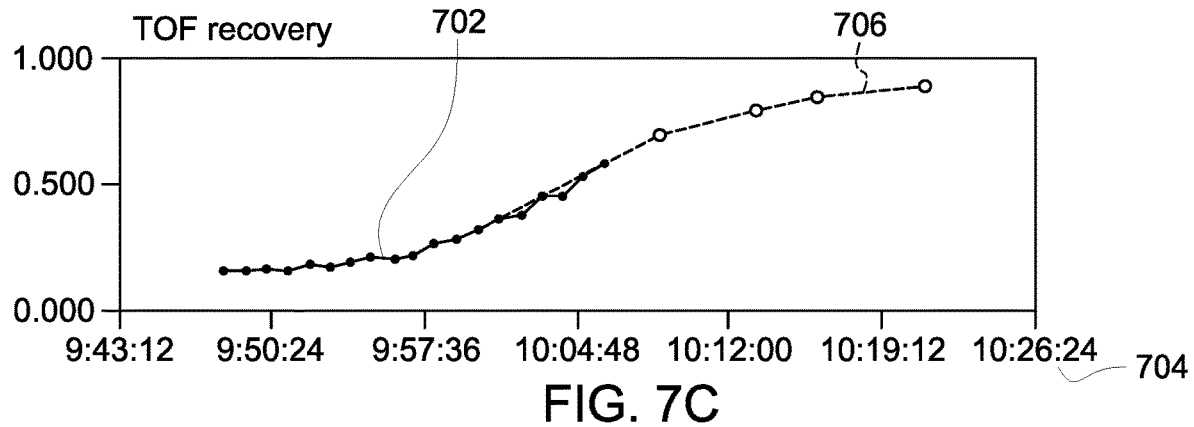
Figure 7D:
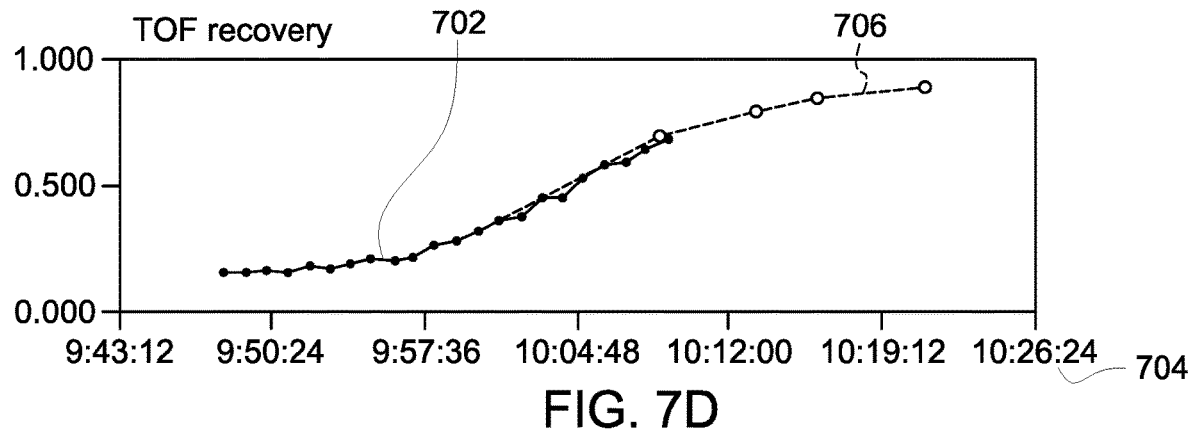
Figure 7E:
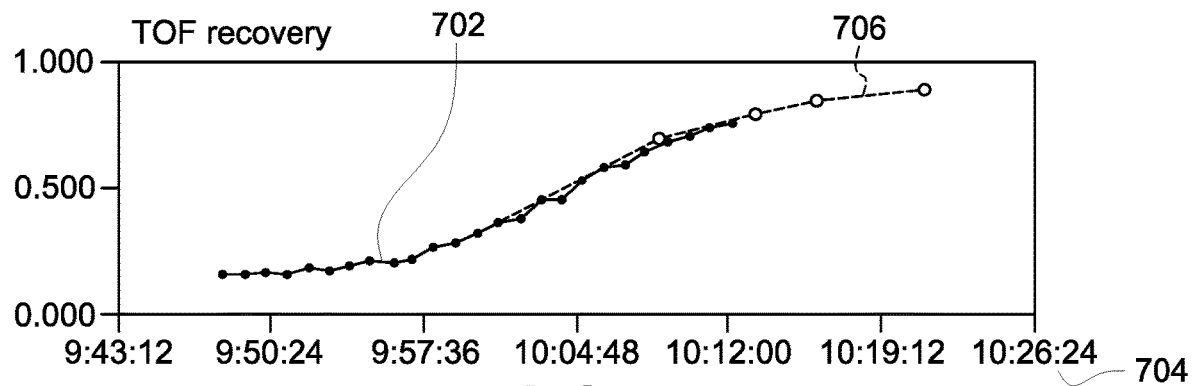
Figure 7F:
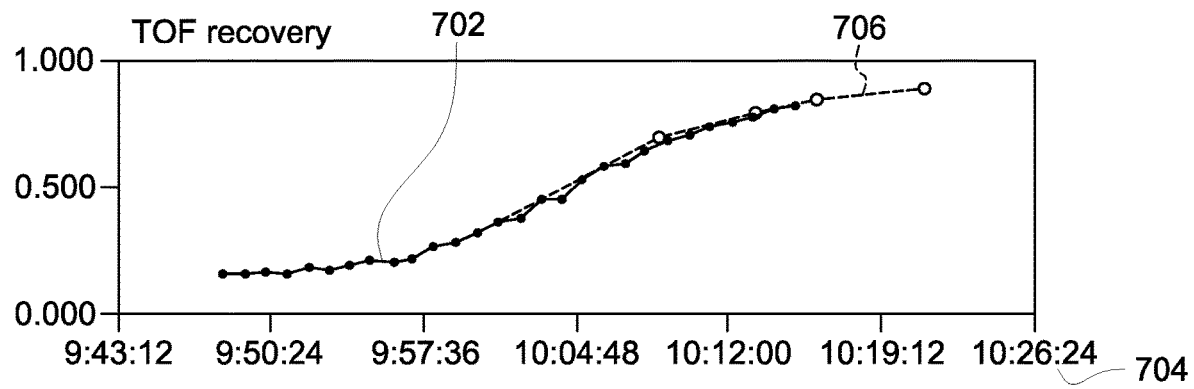
Figure 7G:
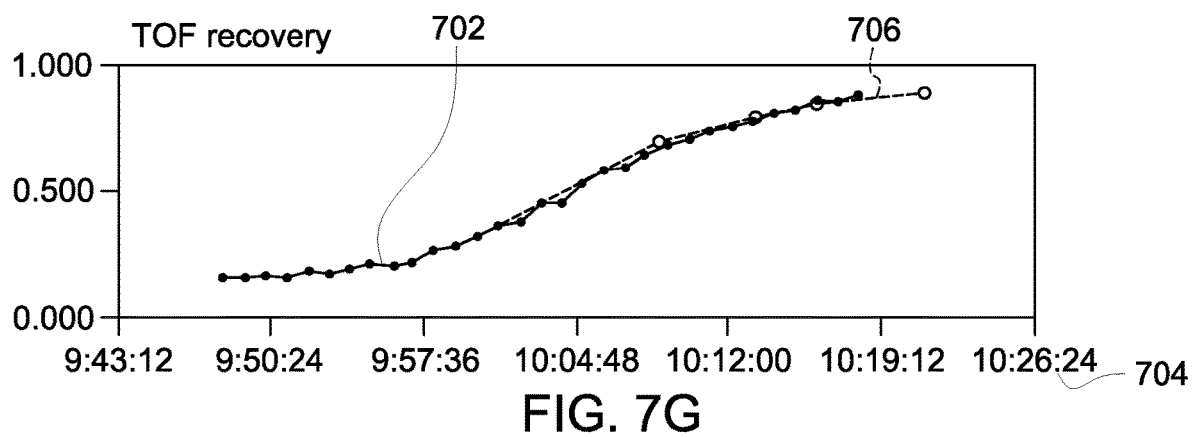
Figure 7H:
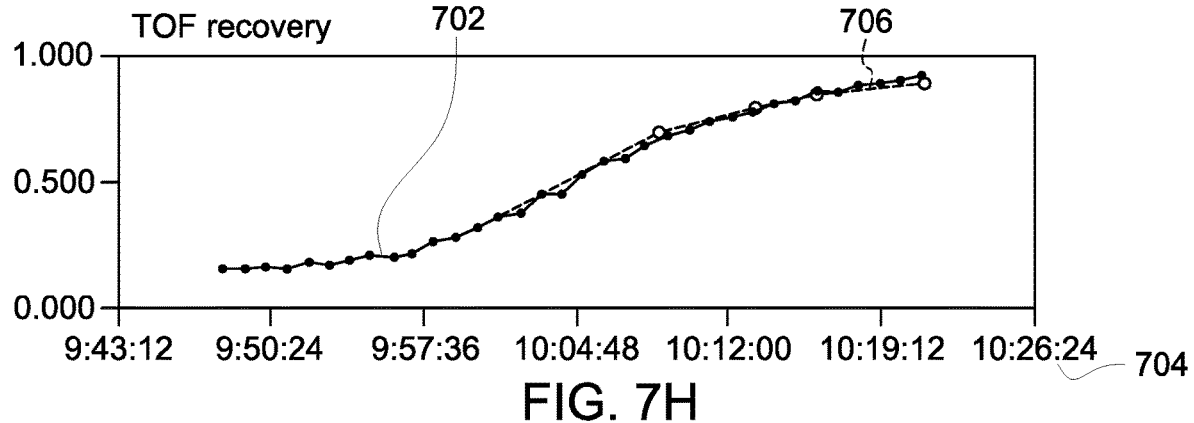
Figure 8:
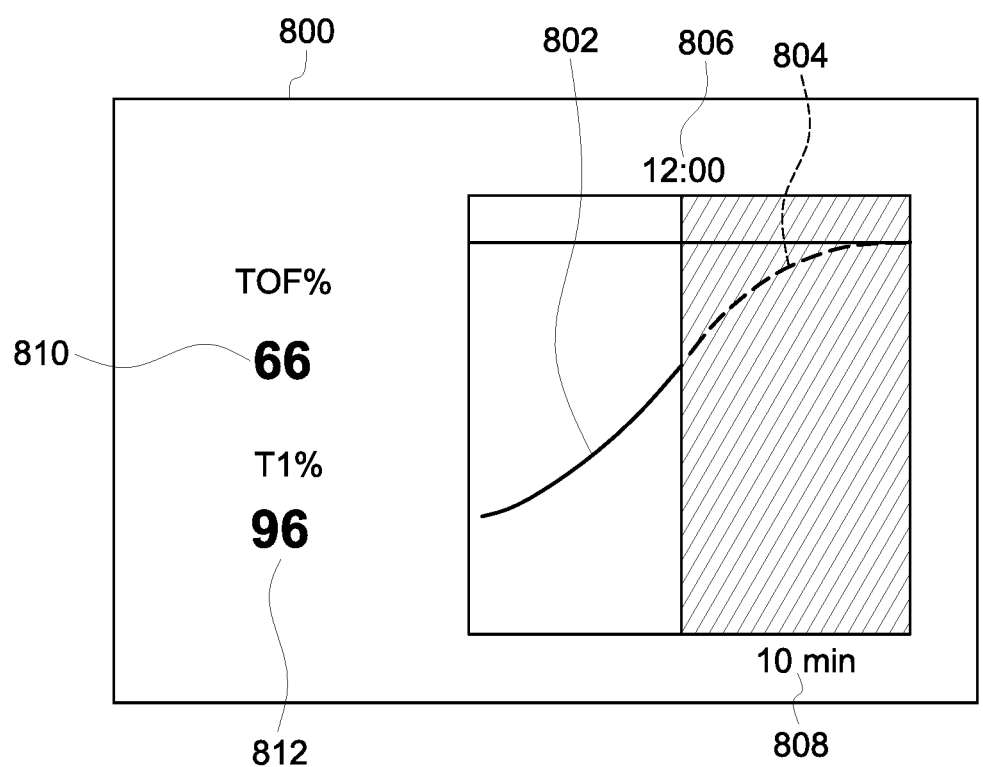
FIG. 8 is a display showing the estimated recovery time and predicted recovery trend.

FIG. 8 illustrates a display 800 that can be presented to the clinician to utilize the predicted recovery time. The display 800 includes similar information as described above with reference to FIG. 7. Specifically, the measured muscle response ratios, such as the TOF ratios 802, obtained from the patient are shown to the clinician relative to a vertical axis that represents the TOF ratio as a percentage and the horizontal time axis. In addition to the measured TOF ratios, the display 800 includes the predicted recovery trend 804 that is separated from the measured TOF trend by visually using different background and trend visualizations. The predicted recovery trend 804 is used to create an estimated recovery time that is shown to the clinician relative to the current time 806. Further, the display 800 includes the predicted recovery time 808 that provides the clinician with the amount of time that needs to run until extubation can occur. In this manner, the clinician is presented with an actual time 806 and the amount of time that needs to pass before extubation can occur. This information allows the clinician to make decisions as to whether to give an antidote, the type of antidote or to allow the patient to recover normally.

The display in FIG. 8 further includes a numeric illustration 810 of the present TOF ratio as well as the T1 percentage 812. The T1 percentage 812 is the ratio of the T1 muscle twitch relative to a reference value. The T1 percentage also provides an indication of how close the patient is to recovery that would allow extubation.

As discussed above, the method and system of the present disclosure creates a predicted neuromuscular recovery trend 804 shown in FIG. 8 that allows for a predicted time when the TOF ratio will exceed a threshold percentage and allow for safe extubation of the patient. The calculation of the predicted recovery trend can be done utilizing a wide variety of different algorithms and recovery models that utilize not only measurements taken from the patient during TOF stimulation but also based upon data obtained from historical patient groups. Based upon data analysis and the study of recovery time, common trends and recovery graph shapes have been identified for patients in patient groups similar to the patient being monitored. The shape of the TO2 and TOF trend curves determined over a large patient group can be utilized to generate the predicted recovery trend for the patient being monitored and thus implemented utilizing measured values from the actual patient.

In one contemplated example, before T4 responses and TOF ratios are available, train-of-two (TO2) ratios can be calculated for a patient. These TO2 ratios can then be utilized to initialize a model to create the recovery trend for the patient. As the patient continues to recover, the predicted recovery trend can be compared to measured muscle response ratios, such as the TO2 ratios and/or measured TOF ratios from the patient. Based upon this predicted recovery trend, an estimated recovery time is determined and shown to the clinician in a display similar to the display 800 shown in FIG. 8. Although this is one type of estimation method for predicting the estimated recovery time, various different methods and recovery trend models and algorithms are contemplated as being within the scope of the present disclosure.

During the normal recovery process, such as shown in the graphic illustration in FIG. 8, the predicted recovery trend is an extension of the measured recovery trend 802 determined from the measured TOF ratios. However, if, during the recovery process, additional amounts of a neuromuscular blocking agent (NMBA) is administered to the patient, the measured trend values that are based upon muscle twitches in response to the series of stimulations will vary greatly from the predicted trend values. Additionally, if a reverse NMBA is given to the patient, the actual measured trend values will also vary in the opposite direction from the predicted trend values for that measurement time in the recovery. Since these types of changes affect both the predicted recovery trend and recovery time estimate 808, the present inventors have recognized that the measured trend values and muscle response ratios obtained from the patient should be monitored continuously during the operation when NMT is measured. It was found necessary that in order to react to sudden changes in the measured recovery trend and to update the recovery models and recovery time estimates appropriately, monitoring measured recovery trend needs to occur continuously.

Figure 9A:
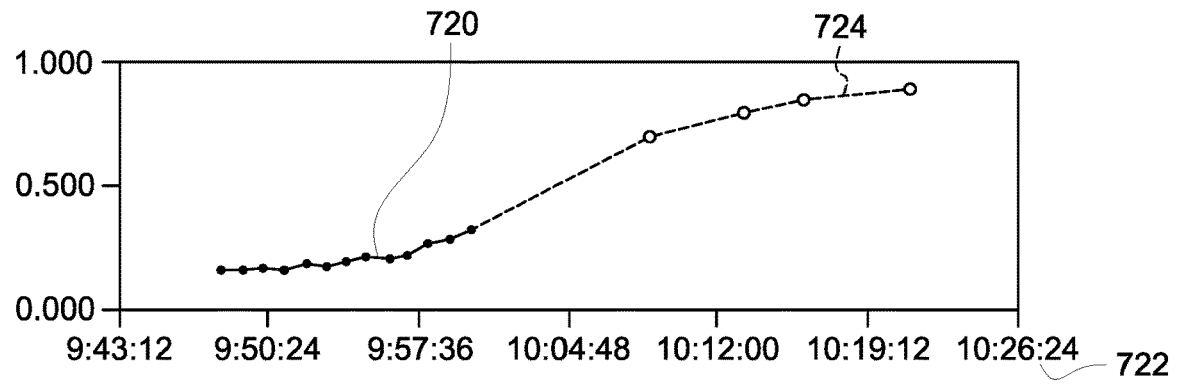
FIGS. 9A-9B are a series of graphs showing a rapid decrease in the measured ratios at several measurement times relative to a predicted recovery trend.

FIG. 9A, like FIG. 7A discussed previously, illustrates a display that is presented to a clinician that includes a series of measured ratios 720 that are obtained from the patient at regularly spaced measurement times and are plotted along the time axis 722. The series of individual measured ratios 702 begin to rise as the depth of relaxation lessens. As indicated in the prior description, a predicted recovery trend 724 is calculated based on a recovery model that is initialized with initial model parameter values and at least one ratio measured from the patient indicating the beginning of recovery. The predicted recovery trend 724 is displayed along the time axis after the last of the measured ratios 720 from the patient. As discussed previously, the estimated ratios determined from the trend curve 724 will exceed 90% at approximately the time 10:21:16. The predicted recovery trend was generated by the system utilizing at least one measured ratio from the patient and one of multiple different types of recovery models for the TO2 and TOF ratios, such as utilizing a sigmoid function. As has been determined by the inventors, the recovery trend from a NMBA resembles an s-shape and one contemplated model is a sigmoid-based model to predict both TO2 and TOF ratios and subsequent measurement times. The recovery model is based on selected model recovery trends and updated based on the selected model recovery trends and the recovery trend information from the patient. Although a sigmoid-based function is contemplated as the selected recovery model, other models could be used for creating the predicted recovery trend 724.

Figure 9B:
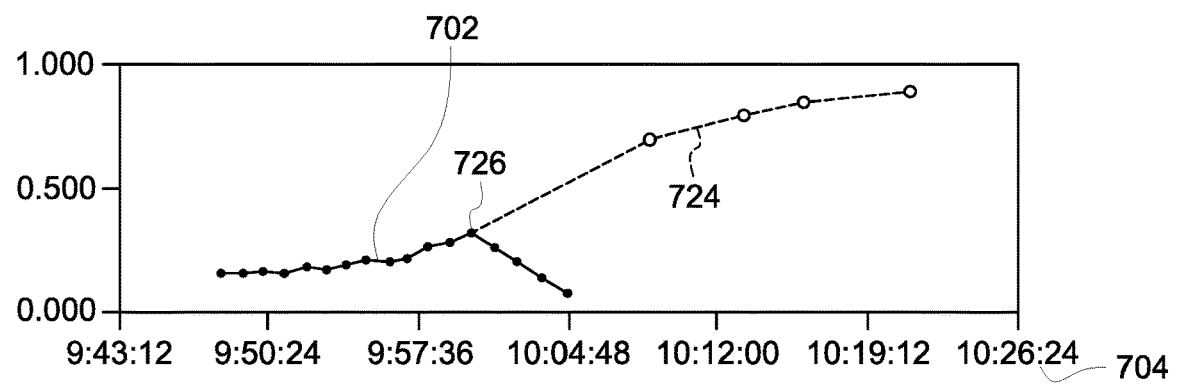

Referring now to FIG. 9B, there shown is a dramatic change in the measured recovery trend 720 as a result of application of an NMBA to the patient during the monitored recovery, such as at a time indicated by reference numeral 726. As can be seen by the difference between the predicted recovery trend 724 and the actual, measured recovery trend 720, the two curves begin to deviate substantially at each measurement time immediately after the application of the NMBA at time 726. Since the administration of the NMBA substantially reduces the response ratio, the predicted recovery time calculated utilizing the predicted recovery trend 724 will no longer be valid or accurate. In accordance with the method of the present disclosure, the method detects this sudden change in the measured recovery trend and identifies the change as being a result of the administration of an NMBA. At this time, it is possible to end the recovery prediction process and restart the prediction process once the recovery trend starts to rise again. In either case, the predicted recovery time will be modified and will be indicated to the clinician such that the clinician can take the required steps and continue to monitor the patient process.

In accordance with the present disclosure, the measured muscle response ratios, such as the TOF or TO2 ratios, are monitored and calculated from the patient at regularly spaced measurement times during the recovery process. Once the trend begins to rise, indicating the beginning of recovery from the NMBA, the recovery prediction process can begin and the predicted recovery trend is calculated. The measured ratios from the patient are obtained at the measurement times and the actual, measured trend values are compared to predicted trend values at each of the measurement times. Based on the differences between the predicted trend values and the measured trend values, the method of the present disclosure can determine if an NMBA or reverse NMBA has been administered. Typically, this determination will occur based either comparing the magnitude of the difference to a threshold value or limit or if the ratios exceed a lesser threshold for a number of consecutive measurement times. The value for the limit and the number of measurement times can be selected depending on the desired sensitivity for the system and method.

Figure 10A:
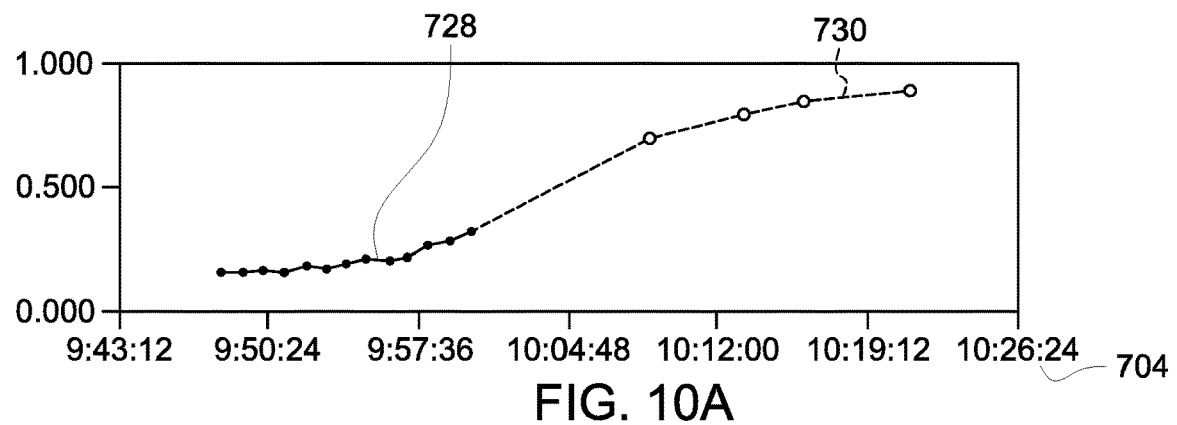
FIGS. 10A-10B are a series of graphs showing a rapid increase in the measured ratios at several measurement times relative to a predicted recovery trend.
Figure 10B:
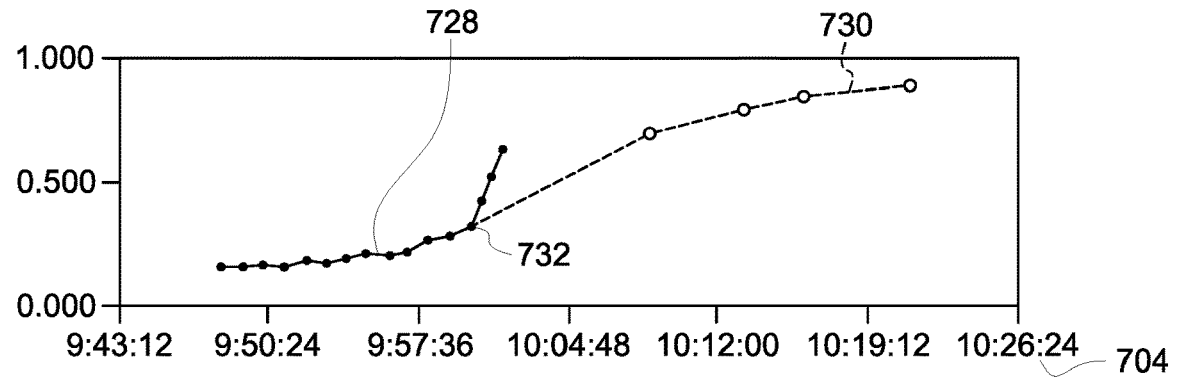

FIG. 10A is similar to FIG. 9A in which the predicted recovery trend 730 is shown with the series of individually measured ratios 728 taken at each of the spaced measurement times. FIG. 10B illustrates the change in the measured ratios 728 from the patient after the application of a reverse NMBA at time 732. Since the application of the reverse NMBA causes an acceleration in the recovery of the patient, the measured ratios begin to increase at a rate that is much greater than the predicted recovery trend 730. In accordance with the method of the present disclosure, when the method detects the rapid increase in the measured ratio as compared to the predicted ratios following the administration of the reverse NMBA at time 732, the method again determines that the predicted recovery time will no longer be accurate. Based upon the determination of the rapid increase in the ratio after time 732, the method could either continue the recovery prediction process utilizing another model, such as a linear model, instead of the sigmoid model or end the operation of the recovery prediction process. If the process continues, the linear recovery estimation model could be utilized since it can better approximate the patient recovery following the administration of the reverse NMBA. If the estimation is ended, the clinician will need to monitor the measured ratio manually and determine when the measured ratio exceeds the extubation threshold. Since the clinician administered the reverse NMBA and recovery is occurring very rapidly, the clinician will be able to manually monitor the recovery and extubate the patient at the desired time.

As indicated in FIGS. 9A and 9B, the predicted recovery trend 724 is calculated prior to beginning the recovery prediction process based upon prior patient information utilizing modeling algorithms and models. However, once the method detects the administration of additional NMBA, such as at time 726, the system and method of the present disclosure can modify the model used to generate the predicted recovery trend 724 by utilizing the actual measurements made from the patient and the calculated ratios before the administration of the NMBA, such as illustrated by the ratios 720 shown in FIG. 9A. By modifying the model utilizing prior measurements and ratios during a previous measurement cycle, the system and method of the present disclosure can create a model that is not only based upon historic trends, but also is based upon data obtained from the patient utilizing the same or similar NMBA. By updating model parameter values utilizing patient data obtained from the patient during the past recovery rise, the method and system of the present disclosure can optimize the recovery prediction model used to create the predicted recovery trend 724 and provide a better estimation of the predicted extubation time.

In the embodiment shown in FIG. 9B, if the recovery prediction process is restarted, the prediction process will again restart when the obtained ratios from the patient begin to show recovery in either the TOF ratio or the TO2 ratio. Once the recovery prediction process restarts, the predicted recovery trend 724 can again be calculated and displayed to the clinician along with a predicted recovery time.

In an alternate embodiment, the recovery prediction process can be placed in a paused state, which may be necessary in a scenario in which there is a sudden but quick change in the trend, which may result from reasons other than the administration of NMBA or a reverse NMBA. Further, if a NMBA or reverse NMBA is administered, the typical first action would be to pause the recovery prediction process. If the monitored trend does not return to normal within a specified delay period, the recovery prediction process is ended. During the pause period, the ratios 720 are monitored and compared to the predicted trend values. If the measured trend values return to normal, the previous model can be used or a new model calculated utilizing previous patient data. In case NMBA is given to the patient and it is detected as a result of monitoring the trend, the predicted recovery time will be later than originally calculated based on the administration of additional NMBA.

As can be understood by the above description and the FIGS. 9A-9B and 10A-10B, the recovery trend is monitored continuously at regularly spaced measurement times and, when the measured trend values vary either substantially above or substantially below the predicted trend values determined from the measured recovery trend, determinations of whether an NMBA or a reverse NMBA has been administered to the patient can be made and the recovery prediction process, depending on the situation, either started, paused, ended, or restarted.

Figure 11:
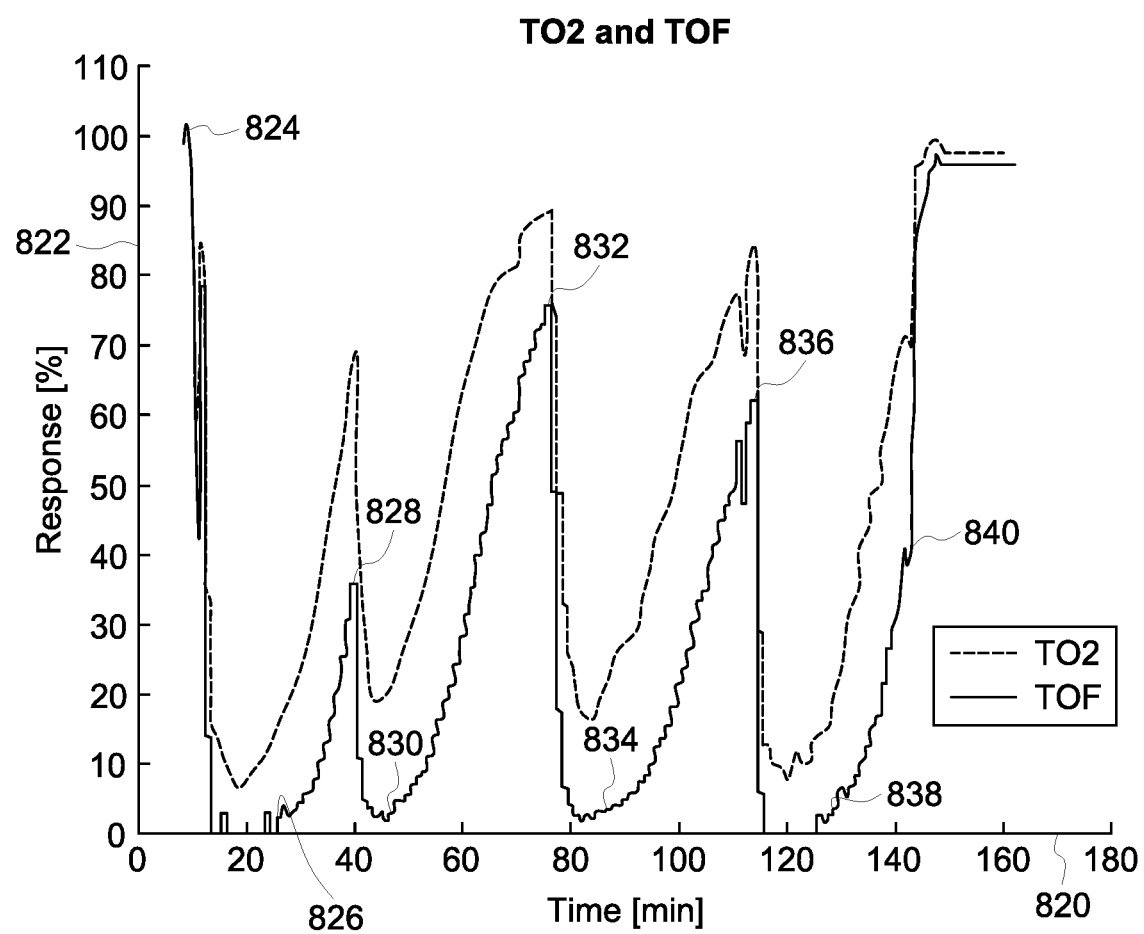
FIG. 11 is a graph illustrating the monitoring of a patient and the measured ratios during a surgical procedure.

FIG. 11 is an example of possible changes in the recovery trend when the patient is medicated several times with NMBA and once with a reverse NMBA. In the graph of FIG. 11, both the TO2 and TOF are shown and are used in the recovery prediction process. Muscle response ratios can be used to derive trend values that describe the recovery process and that can be used in monitoring the measured recovery trend. In the graph shown in FIG. 11, the running time is shown along the horizontal axis 820 while the response ratio (percentage) is shown along the vertical axis 822. In the particular case shown in FIG. 11, the patient is initially medicated with NMBA at time 824. The effect of the initial NMBA bolus can be seen when the muscle response ratios of TO2 and TOF start to decrease from 100% very rapidly. In the graph shown in FIG. 11, the first recovery prediction process begins at point 826 at which time the TOF begins to rise, thereby indicating patient recovery. The recovery prediction process continues until point 828 when a second bolus of NMBA is given to the patient. When the second bolus is given to the patient at point 828, the response percentage immediately drops as can be clearly seen by the fall of the TO2 and TOF ratios. Due to the fall detected in the recovery trend, the recovery prediction process is terminated.

After the delivery of the second bolus of NMBA, the second recovery prediction process begins at point 830, which is when the measured muscle response ratios and trend values again indicate patient recovery. Since both TO2 and TOF ratios were measured from the patient prior to the beginning of the second recovery prediction process at point 830, the recovery model used to predict recovery time can either be based simply on initial model parameters or can be updated utilizing model parameter values that were obtained from the patient during the first recovery prediction process.

The recovery prediction process continues until point 832, at which time a third bolus of NMBA is given to the patient, thus causing another rapid decrease in the TO2 and TOF ratios. Once again, after detecting this sudden fall in the response percentage, the recovery prediction process is terminated.

A third recovery prediction process begins at point 834 where the recovery model used to create the predicted recovery trend can either utilize initial model parameter values or can be updated to include parameter values obtained from the patient during previous measurement from the patient during the surgical procedure. The recovery prediction process again continues until point 836 at which time a fourth bolus of NMBA is applied to the patient, thus causing another dramatic decrease in both the TO2 and TOF ratios. The fourth and final recovery prediction process begins at point 838.

During this portion of the recovery process, a reverse NMBA bolus is applied to the patient at point 840, which causes a dramatic and rapid increase in the TO2 and TOF ratios until both ratios reach the recovery threshold. When the reverse NMBA bolus is supplied to the patient, the original recovery model may no longer be accurate in estimating the recovery time. In such a case, the recovery estimation process could be terminated or another recovery model selected, such as a linear model. A linear recovery model could better represent patient recovery expedited with reverse NMBA and thus, provide more accurate recovery time estimations.

The purpose of the patient case shown in FIG. 11 is to illustrate in practice how the medication affects the recovery trend of a patient, how important monitoring the trend is during recovery and how the recovery prediction process of the present disclosure could be used in this type of a case.

Figure 12:
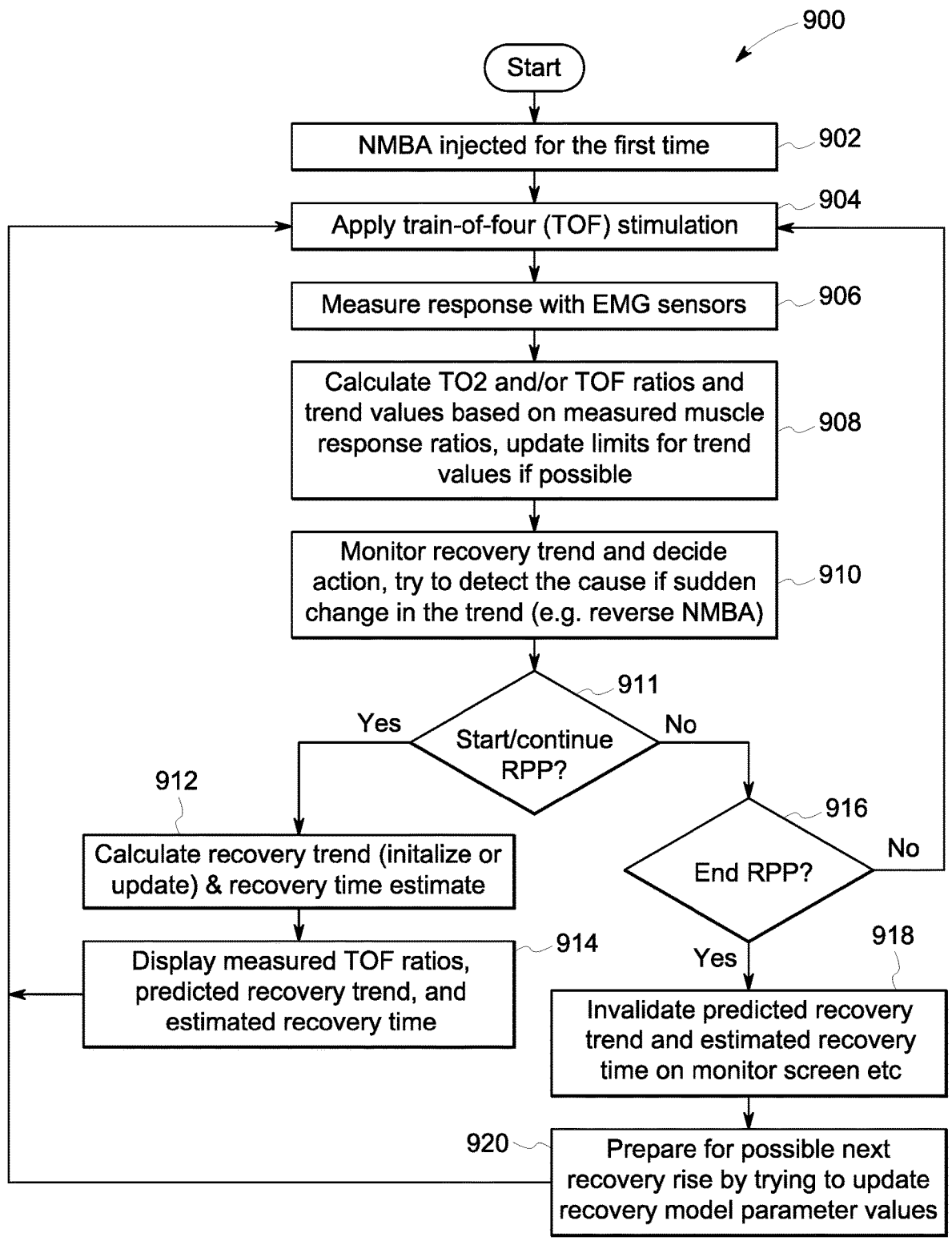
FIG. 12 is a flowchart illustrating one method of operating the system and method of the present disclosure.

FIG. 12 illustrates one method of operating the patient monitoring system in accordance with the present disclosure. As indicated in FIG. 12, the method begins with a neuromuscular blocking agent (NMBA) being injected in the patient in step 902. After the NMBA has been injected and begins to act, the patient needs to be continuously monitored during the surgical procedure.

At the end of the surgical procedure when the NMBA is being reduced and counteracted, the method begins to apply TOF stimulation to the patient in step 904. As described previously, TOF stimulation is one type of common monitoring used to determine depth of relaxation and to determine when a patient can be safely extubated. In step 906, the method measures the response of the patient to the TOF stimulation utilizing the EMG sensors 160 shown in FIG. 1. The application of the TOF stimulation in step 904 and the measurement of the responses in step 906 is a common procedure and generates the curves shown in FIG. 2. After the responses have been measured in step 906, the microcontroller of the neuromuscular transmission monitor 110 calculates standard values, such as the TOF ratio, the TO2 ratio, as well as any trend values that are based on the measured muscle response ratios. In this step, limits for the trend values that will be used in monitoring the patient recovery can be updated if possible. The limits are the predetermined changes that are deemed acceptable between the measured trend and a predicted trend determined using the method of the present disclosure.

In step 910, the system monitors the recovery trend that is determined from the measured muscle response ratios obtained from the patient. The recovery trend determined from actual ratios obtained from the patient is monitored to determine if there has been a sudden change in the monitored trend values, which may occur due to the delivery of a NMBA or a reverse NMBA. As indicated previously with reference to FIG. 11, the delivery of either additional NMBA or a reverse NMBA causes the monitored trend to deviate from a predicted trend developed using a recovery model.

In step 911, the system determines whether the recovery prediction process can continue or should be restarted based on the monitoring that occurred in step 910. For example, if there has not been a sudden change in the monitored trend values, the recovery prediction process can continue and the method proceeds to step 912. However, if a sudden change has been detected, the system proceeds to step 916, where the system determines whether the recovery prediction process should be ended, as will be described in greater detail below.

If the system determines in step 911 that the recovery prediction process should start or continue, the system movers to step 912. In step 912, the method calculates a predicted recovery trend based upon the calculations made in step 908 and based upon a recovery model that utilizes initial model parameter values that could possibly be based upon historic patient trend data. As discussed in previous portions of the present application, the predicted recovery trend calculated in step 912 can be calculated utilizing a variety of different types of recovery models, algorithms and data analysis techniques. One possible recovery model is a sigmoid model that utilizes model parameter values and at least one TO2 or TOF ratio calculated as recovery begins.

Once the predicted recovery trend is determined in step 912, the method moves to step 914 in which the measured TOF ratios and the predicted recovery trend are displayed, such as shown in FIG. 8. The display shown in FIG. 8 can also include an estimated recovery time. In this manner, the system and method of the present disclosure provides the clinician with not only the actual measured TOF ratios but also a predicted recovery trend and an estimated time to recovery in step 914. Based upon all of this information, the clinician can then make treatment decisions, such as to administer an antidote, what type of antidote to administer or whether to allow the patient to recover under normal circumstances.

After completing step 914, the system returns to step 904 and the next train-of-four (TOF) stimulation is applied to the patient and the method continues as described. The system thus continues to monitor the recovery trend from the patient and determines if the monitored recovery trend varies from a predicted recovery trend. If the variation between the two trends remains below preselected limits, the system continues to provide a predicted recovery time. However, if the system determines that the monitored recovery trend is outside of the preselected limits, the system makes a decision in step 911 as to whether the recovery prediction process can continue.

If the system and method determines in step 911 that the recovery prediction process should not continue, the system proceeds to step 916 and a determination is made as to whether the recovery prediction process should end. If the recovery prediction process should pause instead, the system returns directly to step 904 and the next TOF stimulation is applied to the patient and the process continues.

However, if the system determines in step 916 that the recovery prediction process should end, such as due to the administration of a reverse NMBA, the system moves to step 918 where the predicted recovery trend and the estimated recovery time can be invalidated. This invalidation could result in a message on the patient monitor to alert the clinician about the change in recovery time. After alerting the clinician and invalidating the predicted recovery trend and recovery time, the system moves to step 920 where the system prepares for the next recovery rise. The next recovery rise will indicate the patient recovering from the NMBA. In preparation for this recovery, the system and method can update the recovery model parameter values based on prior measurements from the patient before the dramatic change in the recovery trend of the patient detected in step 910. As described in detail previously, the recovery model can be updated based on prior measurements from the patient to enhance the accuracy of the recovery model.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their object.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

We claim:

1. A method to estimate recovery time of a patient from neuromuscular block (NMB), comprising:
    applying a first series of stimulations to a nerve of the patient at a first measurement time;
    measuring a plurality of muscle twitches in response to each of the first series of stimulations;
    calculating a muscle response ratio based on the measured muscle twitches in response to the first series of stimulations;
    utilizing a recovery model and the calculated muscle response ratio from the patient to generate a predicted recovery trend for the patient;
    monitoring subsequent trend values measured from the patient based on muscle twitches measured in response to subsequent series of stimulations applied to the patient;
    comparing the subsequent measured trend values to the predicted recovery trend; and
    selectively modifying the predicted recovery trend based on the comparison,
    wherein the estimation method is restarted when a measured trend value, from among the monitored subsequent trend values, at a measurement time is below the predicted recovery trend by more than a predetermined limit.

2. The method of claim 1 further comprising the step of estimating a recovery time based on the predicted recovery trend.

3. The method of claim 2 further comprising the step of modifying the estimated recovery time based on the comparison of the subsequent measured trend values to the predicted recovery trend.

4. The method of claim 1 wherein the step of comparing the subsequent trend values to the predicted recovery trend includes detecting changes from the recovery model that are a sign of a medication change of the patient.

5. The method of claim 4, wherein modifying the predicted recovery trend includes modifying the recovery model to reflect the medication change.

6. The method of claim 5 wherein the medication change is an additional dose of NMB.

7. The method of claim 5 wherein the medication change is an NMB antagonist.

8. The method of claim 1 wherein the first series of stimulations and the subsequent series of stimulations are train-of-four (TOF) stimulations and the calculated trend values are derived from train-of-two (TO2) or TOF ratios.

9. The method of claim 1 wherein the recovery model is a sigmoid model that utilizes initial model parameter values based on historical patient data and the calculated muscle response ratio obtained from the patient.

10. The method of claim 1 wherein the estimation method is ended when a measured trend value from the patient at a measurement time exceeds the predicted recovery trend by more than a predetermined limit.

11. The method of claim 1 wherein the predicted recovery trend is modified based upon measured recovery trend of the patient before restarting the estimation method.

12. The method of claim 2 wherein the estimated recovery time occurs when the predicted recovery trend exceeds a recovery threshold.

13. The method of claim 1 further comprising the steps of:
    determining the subsequent trend values at each of the measurement times until a measured recovery trend exceeds a recovery threshold;
    comparing the measured trend values derived from the muscle response ratios to the predicted recovery trend at each measurement time; and
    alerting a user when the determined subsequent trend value differs from the predicted recovery trend for the measurement time by more than an alarm limit.

14. A method to monitor recovery trend and estimate recovery time of a patient from neuromuscular block (NMB), comprising:
    applying a first train-of-four (TOF) stimulation to a nerve of the patient at a first measurement time;
    measuring a plurality of muscle twitch responses in response to the first TOF stimulation;
    calculating trend values based on a ratio of the measured muscle twitch responses at the first measurement time;
    utilizing a recovery model with initial parameter values to generate a predicted recovery trend for the patient;
    predicting a recovery time based on when the predicted recovery trend will reach a recovery threshold;
    monitoring subsequent trend values measured from the patient based on muscle twitch responses measured in response to subsequent series of TOF stimulations applied to the patient at a plurality of subsequent measurement times;
    comparing the subsequent trend values to the predicted recovery trend; and modifying the estimated recovery time based on a difference between the determined subsequent trend values and the predicted recovery trend, wherein the monitoring and estimation method is restarted when a measured trend value, from among the monitored subsequent trend values, at a measurement time is below the predicted recovery trend by more than a predetermined limit.

15. The method of claim 14 wherein the recovery model is a sigmoid model that utilizes initial model parameter values and at least one of a TO2 or a TOF ratio obtained from the patient.

16. The method of claim 14 wherein the estimation method is ended when a measured trend value from the patient at one of the plurality of subsequent measurement times exceeds the predicted recovery trend by more than a limit.

17. The method of claim 14 wherein the estimation method is ended when a measured trend value from the patient at one of the plurality of subsequent measurement times is below the predicted recovery trend by more than a limit and subsequently restarted when patient recovery is detected based on the muscle twitch responses.

18. The method of claim 17 wherein the predicted recovery trend is modified based upon a measured recovery trend based on either a TO2 or a TOF ratio acquired from the patient before restarting the estimation method.

19. A medical device for monitoring depth of relaxation of a patient, comprising:
- a stimulator operable to apply train-of-four (TOF) stimulations to a nerve of the patient at a plurality of measurement times;
- an electromyography (EMG) sensor operable to detect a first muscle twitch, a second muscle twitch, a third muscle twitch and a fourth muscle twitch in response to the TOF stimulations at the plurality of measurement times;
- a controller operable to calculate muscle response ratios and trend values at each of the plurality of measurement times and to create a predicted recovery trend based on a recovery model and the calculated trend values, wherein the predicted recovery trend indicates a predicted recovery time;

wherein the controller is operable to calculate subsequent measured trend values at each of the plurality of measurement times and to compare each of the plurality of subsequent measured trend values to predicted trend values for the measurement time and to react to sudden changes in the measured trend values and to start, continue, pause, or end recovery prediction process, and update the predicted recovery trend, and recovery time estimate, and wherein the controller is configured to restart the process of calculating muscle response ratios and trend values at each of the plurality of measurement times and creating a predicted recovery trend based on the recovery model and the calculated trend values when a measured trend value, from among the monitored subsequent trend values, at a measurement time is below the predicted recovery trend by more than a predetermined limit.

* * * * *